United States Patent
Cook et al.

(10) Patent No.: US 6,706,490 B1
(45) Date of Patent: Mar. 16, 2004

(54) METHOD FOR DETECTING RHEUMATOID ARTHRITIS EMPLOYING THE CB10 PEPTIDE OF MAMMALIAN TYPE II COLLAGEN AS AN ANTIGEN

(75) Inventors: Andrew Cook, Nunawading (AU); Merrill Rowley, Camberwell (AU); Ian Mackay, Malvern (AU)

(73) Assignees: Montech Medical Developments Pty. Ltd., Melbourne (AU); Rondole Pty. Ltd., Hobart (AU)

( * ) Notice: Subject to any disclaimer, the term of this patent is extended or adjusted under 35 U.S.C. 154(b) by 0 days.

(21) Appl. No.: 09/623,497

(22) PCT Filed: Mar. 18, 1998

(86) PCT No.: PCT/AU98/00176

§ 371 (c)(1),
(2), (4) Date: Nov. 20, 2000

(87) PCT Pub. No.: WO98/41865

PCT Pub. Date: Sep. 24, 1998

(30) Foreign Application Priority Data

Mar. 19, 1997 (AU) .......................................... P05712/97

(51) Int. Cl.[7] ........................ G01N 33/53; G01N 33/564
(52) U.S. Cl. .............................. 435/7.92; 435/4; 435/5; 435/6; 435/7.1; 435/7.21; 435/7.2; 435/7.22; 435/7.23; 435/7.31; 435/7.32; 435/7.36; 435/7.4; 436/57; 436/172; 436/501; 436/504; 436/528; 436/542; 436/544; 436/545; 436/546; 436/800; 436/804; 436/807; 422/56; 422/61
(58) Field of Search ....................... 435/7, 4, 7.1, 7.21, 435/7.4, 232, 5, 6, 7.2, 7.22, 7.23, 7.31, 7.32, 7.36, 7.92; 436/172, 528, 808, 829, 546, 800, 501, 544, 57, 504, 545, 804, 542, 807; 424/94.5; 422/56, 61

(56) References Cited

FOREIGN PATENT DOCUMENTS

JP 62-12800 A 1/1987

OTHER PUBLICATIONS

Revue du Rhumatisme, 1991, 58(1), pp. 19–24.*
Andersson, M. A., et al., "Analysis of Type II Collagen Reactive T Cells in the Mouse" Scand. J. Immunol, vol. 33, pp. 505–510 (1991).
Miyahara, H., et al., "Identification and Characterization of a Major Tolerogenic T–cell Epitope of Type II Collagen that Suppresses Arthritis in B10.RIII Mice", Immunology, vol. 86, pp. 110–115 (1995).
Nabozny, G.H., et al., "Identification of a Cyanogen Bromide Fragment of Porcine Type II Collagen Capable of Modulating Collagen Arthritis in B10.RIII (H2[1]) Mice[1]", Autoimmunity vol. 20, pp. 39–49.

Kerwar, S.S., et al., "Type II Collagen Induced Arthritis in Rats: Clinical and Immunological Studies", Int. J. Tiss. Reac. vol. VII(6), pp. 409–429.
Rowley, M.J., et al., "Epitope Specificty of Antibodies to Type II Collegan in Rheumatoid Arthritis and Systemic Lupu Erythematosus", Rheumatology International, vol. 12(2), pp. 65–69.
Boissier, M.C., et al., "Role De La Conformation Du Collagenen Dans L'Immunite Anti–Collagene De Type II Au Cours De La Polyarthrite Rhumatoide", Revue du Rhumatisme, vol. 58(1), pp. 19–24 (1991).
Bornstein, P. and Sage, H. (1980). Structurally distinct collagen Types. Ann. Rev. Biochem. 49:957–1003.
Brodsky, B. and Shah, N.K. (1995). The triple–helix motif in proteins FASEB J. 9:1537–1546.
Buckee, C., Morgan, K., Ayad, S., Collins, I., Clague, R.B., Holt, P.J.L. (1990). Diversity of antibodies to type II collagen in patients with rheumatoid arthritis: detection by binding to—chains and to cyanogen bromide peptides. Brit. J. Rheumatol. 29:254–258.
Charriere, G., Hartmann, D.J., Vignon, E., Ronziere, M–C., Herbage D., Ville, G. (1988). Antibodies to types I, II, IX, and XI collagen in the serum of patients with rheumatic diseases. Arthritis Rheum. 31:325–332.
Choi, E.K.K., Gatenby, P.A., McGill, N.W., Bateman, J.F., Cole, W.G., York, J.R. (1988). Autoantibodies to type II collagen: occurrence in rheumatoid arthritis, other arthritides, autoimmune connective diseases, and chronic inflammatory syndromes. Ann. Rheum. Dis. 47:313–322.
Clague, R.B., Shaw, M.J. Holt, P.J.L. (1980). Incidence of serum antibodies to native type I and type II collagen in patients with inflammatory arthritis. Ann. Rheum. Dis. 39:201–206.
Collier, D.H., Kerwhr, S.S., Garovoy, M.R., Fye, K.H., Stobo, J.D. (1984). Anticollagen antibodies and immune response gene products in rheumatoid arthritis. Arthritis Rheum, 27:1201–1209.
Cook, A.D., Rowley, M.J., Stockman, A., Muirden, K.D., Mackay, I.R. (1994). Specificity of antibodies of type II collagen in early rheumatoid arthritis. J. Rheumatol. 21:1186–1191.

(List continued on next page.)

Primary Examiner—Long V. Le
Assistant Examiner—Lisa V. Cook
(74) Attorney, Agent, or Firm—Foley & Lardner (57) ABSTRACT

A predictive test for rheumatoid arthritis comprises the detection of antibodies to collagen in a biological sample from a patient by contacting the biological sample with an antigen comprising the CB10 peptide of mammalian type II collagen, or an antibody-binding fragment or variant thereof, for a time and under conditions for an antibody-antigen complex to form, and detecting the antibody-antigen complex, for example by immunoassay. A diagnostic test kit is also disclosed.

12 Claims, 5 Drawing Sheets

OTHER PUBLICATIONS

Cook, A.D., Rowley, M.J., Mackay, I.R., Gough, A., Emery, P. (1996). Antibodies of type II collagen in early rheumatoid arthritis: correlation with disease progression. Arthritis Rheum 39:1720–1727.

Courtenay, J.S., Dallman, M.J., Dayan, A.D., Martin, A., Mosedale, B. (1980). Immunization against heterologous type II collagen induces arthritis in mice. Nature 283:666–667.

Fujii, K., Tsuji, M., Kitamura, A., Murota, K. (1992). The diagnostic significance of anti–type II collagen antibody assay in rheumatoid arthritis. Int. Orthop. 16:272–276.

Gay, S., Gay R.E. and Miller, E.J. (1980). The collagens of the joint. Arthritis Rheum. 23:937–941.

Gioud, M. Meghlaoui, A., Costa, O., Monier, J.C. (1982). Antibodies of native type I and II collagens detected by an enzyme linked immunosorbent assay (ELISA) in rheumatoid arthritis and systemic lupus erythematosus. Collagen Rel. Res. 2:557–564.

Heinegard, D. and Paulsson, M. (1987). Methods Enzymol. 145:336–363.

Hochberg, M.C. (1981). Adult and Juvenile rheumatoid arthritis: current epidemiologic concepts. Epidemiol. Rev. 3:27–44.

Miller, E.J. (1985). The structure of fibril–forming collagens. Ann. N.Y. Acad. Sci. 460:1–13.

Miller, E.J. and Lunde, L.G. (1973). Isolation and characterization of the cyanogen bromide peptides from the alpha–I(II) chain of bovine and human cartilage collagen. Biochem 12:3153–3159.

Miller, E.J. and Rhodes, R.K. (1982). Preparation and characterization of the different types of collagen. Meth. Enzymol. 82:33–64.

Morgan, K., Clague, R.B., Collins, I., Ayad, S., Phinn, S.D., Holt, P.J.L. (1987). Incidence of antibodies to native and denature cartilage collagens (types II, IX, and XI) and to type I collagen in rheumatoid arthritis. Ann. Rheum. Dis. 46:902–907.

Morgan, K., Clague, R.B., Collins, I., Ayad, S., Phinn, S.D., Holt, P.J.L. (1989). A longitudinal study of anticollagen antibodies in patients with rheumatoid arthritis. Arthritis Rheum. 32:139–145.

Pereira, R.S., Black, C.M., Duance, V.C., Jones, V.E., Jacoby, R.K., Welsh, K.I. (1985) Disappearing collagen antibodies in rheumatoid arthritis. Lancet ii :501–502.

Piez, K.A. (1976). Primary structure. In Biochemistry of collagen. Ramchandran. G.H. and Reddi, A.N. (eds.). Plenum, New York, pp 1–44.

Piez, K.A. (1982). Structure and assembly of the native collagen fibril. Connect Tissue Res. 10:25–36.

Rosenberg, A.M., Hunt, D.W.C., Pretty, R.E. (1984). Antiobodies to native and denatured type II collagen in children with rheumatic diseases. J. Rheumatol. 11:425–431.

Rowley, M.J., Gershwin, M.E., Mackay, I.R. (1988). Collagen antibodies in juvenile arthritis and adult rheumatoid arthritis: differences in levels and type–specificity. J. Rheumatol. 15:289–294.

Rowley, M.J., Mackay, I.R., Brand, C.A., Bateman, J.F., Chan, D. (1992). Epitope specificity of antibodies of type II collagen in rheumatoid arthritis and systemic lupus erythematosus. Rheumatol. Int. 12:65–69.

Scott, P.G. and Veis, A. (1976) The cyanogen bromide peotides of bovine soluble and insoluble collagens. Connect Tissue Res. 4:107–116.

Stuart, J.M., Huffstutter, E.H., Townes, A.S., Kang, A.H. (1983). Incidence and specificity of antibodies to types I, II, III, IV and V collagen in rheumatoid arthritis and other rheumatic diseases as measured by 125 1–radioimmunoassay. Arthritis Rheum. 26:832–840.

Steffen, C., Timpl R. (1963). Antigenicity of collagen and its application in the serologicl investigation of rheumatoid arthritis sera. Int. Arch. Allergy Appl. Immunol 22:333–349.

Stockman, A., Rowley, M.J., Emery, P., Muirden, K.D. (1989). Activity of rheumatoid arthritis and levels of collagen antibodies: a prospective study. Rheumatol. Int. 8:239–243.

Terato, K. Cremer, M.A., Hasty, K. A., Kang, A.H., Hasty, D.L., Townes, A.S. (1985). Physicochemical and Immunological studies of the renatured alpha I(II) chains and isolated cyanogen bromide peptides of type II collagen. Coll. Rel. Res. 5:469–480.

Terato, K., Shimozuru, Y., Katayama, K., Takemitsu, Y., Yamashita, I., Miyatsu, m., Fujii, K., Sagara, M., Kobayashi, S., Goto, M., Nishioka, K., Miyatsaka, N., Nagai. Y. (1990). Specificity of antibodies of type II collagen in rheumatoid arthritis. Arthritis Rheum 33: 1493–1500.

Trentham, D.E.,. Townes, A.S., Kang, A.H. (1977). Autoimmunity to type II collagen: an experimental model of arthritis. J. Exp. Med. 146:857–868.

Trentham, D.E. Kammer, G.M., McCune, W.J., David, J.R. (1981). Autoimmunity to collagen. A shared feature of psoriatic and rheumatoid arthritis. Arthritis Rheum. 24:1363–1369.

Wekmeister, J.A., Ramshaw, J.A. M (1991). Multiple antigenic determinants on type III collagen. Biochem J. 274:895–898.

\* cited by examiner

METHOD FOR DETECTING RHEUMATOID ARTHRITIS EMPLOYING THE CB10 PEPTIDE OF MAMMALIAN TYPE II COLLAGEN AS AN ANTIGEN

FIELD OF THE INVENTION

This invention relates to the diagnosis of rheumatoid arthritis, a chronic disease of the joints and other tissue that is a serious health problem worldwide. In particular, the present invention is directed to providing a predictive test for rheumatoid arthritis in its early stages which shows high specificity and sensitivity, enabling prompt and accurate diagnosis and hence effective treatment with appropriate drugs. Such early treatment can limit irreversible joint damage which is known to occur within the first few years or even months after the onset of rheumatoid arthritis.

BACKGROUND OF THE INVENTION

Rheumatoid arthritis is the most serious of the rheumatic disorders in terms of population prevalence, potential for crippling and morbidity, and life-shortening effects. The disease is characterised by the symmetrical inflammation of multiple joints (polyarthritis). It most frequently affects the small joints of the hands and feet, but inflammation can occur in virtually any joint including spinal joints. Pain, stiffness and swelling of the joints are the main symptomatic features, resulting in loss of function. Damage to the joints leads to serious deformities and functional impairment. Apart from the effects on the joints, rheumatoid arthritis may be associated with a wide range of extra-articular features affecting various organs, such as the heart, blood vessels, lungs and kidneys. Although these extra-articular features are most common in the case of serious forms of rheumatoid arthritis, they may also provide the first symptom of the disease. There is at present no reliable cure for rheumatoid arthritis. Treatment is essentially directed towards alleviating the discomfort caused by the symptoms and arresting the progression of the disease. Sometimes, however, the disease appears to resolve spontaneously, or in response to one or other of the drug regimens currently employed.

Rheumatoid arthritis generally appears after puberty. The prevalence rises with age, and it is 2–3 times more frequent among women than men. The prevalence of definite rheumatoid arthritis is between 1–2% in the majority of white populations (Hochberg, MC, 1981), and the treatment of patients with rheumatoid arthritis consumes a significant component of the health care budget.

Rheumatoid arthritis is included among the autoimmune diseases. Many authors assume that exposure to an infectious agent, bacterium or virus, can initiate rheumatoid arthritis in individuals with a genetic predisposition to the disease. The actual disease is generated by an abnormal reaction of the immune system, which then plays a central role in the progression of articular damage and extra-articular lesions. Since no infectious agent has in fact been convincingly implicated in the disease, rheumatoid arthritis may be a spontaneously occurring autoimmune process, in which the primary response is to an autoantigenic component of the joint itself, rather than to an extrinsic infectious agent.

The idea that rheumatoid arthritis is an autoimmune response to a component of cartilage is traced back to Steffen and Timpl (1963) who first showed antibodies to collagen in rheumatoid arthritis and proposed that rheumatoid arthritis results from an autoimmune response to the collagen molecule present in cartilage now know to be type II collagen. This idea is strongly supported by the observation that immunization with type II collagen induces an arthritis with similarities to human rheumatoid arthritis in appropriate strains of rats, mice or primates (Courtney et al 1980, Trentham et al, 1977).

In human rheumatoid arthritis, autoantibodies to native and denatured type II collagen are detectable in the serum and synovial fluid of up to 30% of patients according to data derived from cross-sectional studies on patients with generally long-standing disease (Morgan et al, 1987; Terato et al, 1990; Rowley et al, 1992). However, the importance of such antibodies to type II collagen has long remained controversial in view of their low frequency in most reported studies, the lack of correlation between antibody levels and disease status (Clague et al, 1980b Stuart et al, 1983; Collier et al, 1984; Morgan et al, 1989; Stockman et al, 1989) and the reported presence of these antibodies in a range of disease other than rheumatoid arthritis (Clague et al, 1980; Trentham et al, 1981; Gioud et al, 1982; Rosenberg et al, 1984; Charriere et al, 1988; Choi et al, 1988; Rowley et al, 1988, 1992). As mentioned, most of the positive associations of about 30% between antibodies and disease have been based on patients with rheumatoid arthritis of long duration. More recently, several studies have shown that the frequency of autoantibodies to type II collagen may be as high as 60–75% in patients tested very early in the course of rheumatoid arthritis, and levels of autoantibody tend to fall as the disease progresses to levels ascertained in the earlier cross-sectional studies (Pereira et al, 1985; Fujii et al, 1992, Cook et al, 1994, 1996). Accordingly, it has been proposed that antibodies to collagen will provide a useful predictive marker of early rheumatoid arthritis and particularly so for those patients in whom rapid progression to joint destruction will occur.

The main structural proteins of the connective tissue in the body are collagens, of which at least 19 genetically different types have so far been described (Brodsky and Shah, 1995). The types of collagen found in a specific tissue are related to the function of the tissue, and they have specific distributions within individual tissues. Articular cartilage in mature joints contains a number of different collagen types, of which type II collagen is the most abundant. It is the major fibrous collagen in all hyaline cartilage and represents 80–90% of the collagen content. Its role is to build up a fibrous network which, together with proteoglycans and hyaluronan, creates an extremely strong structure with the capacity to withstand high pressures (Heinegard and Paulsson, 1987). Type II collagen is a highly conserved molecule between species. It consists of 3 identical a chains, and is moderately glycosylated (Miller, 1985). It is restricted to cartilage and few other tissues, these being the vitreous humour of the eye, and intervertebral discs, in contrast to the more universal distribution of type I and III collagens (Gay et al, 1980).

In general, the basic structure of all native collagen consists of three polypeptide α-chains in the form of a triple helical domain(s) with repeating glycine-X-Y triplets, in which X is often proline and Y is often hydroxyproline (Piez, 1982). Hydroxyproline is essential for the formation of hydrogen bonds that stabilize the helix. Each α-chain is coiled into a tight left-handed helix which averages about 3 amino acid residues per twist. Three α-chains coil about one another in a right-handed manner to create a 300 nm long, 1.5 nm thick, superhelix which is stabilized by hydrogen bonds formed between the α-chains. About 25 to 30 amino acid residues are required on each chain to complete one turn of the superhelix. Heat denaturation of collagen molecules at 45° C. leads to unfolding of the triple helix to display the linear sequence of amino acids along the length of the individual α-chains.

Collagen is stabilized by the formation of covalent cross-links. Two kinds of cross-links are formed in the collagen fibre, intra- and inter- molecular. Cross-link formation involves enzymatic conversion of lysine and hydroxylysine residues, to allysine and hydroxyallysine respectively, by peptidyl lysine oxidase. Allysine and hydroxallysine react with each other, or with lysine, spontaneously, to form aldol and aldimine condensation products. No enzyme catalysis is required for this process, only the physical proximity of the appropriate side chain (Miller, 1985). Cross-links are formed between a modified lysyl or hydroxlysyl residue in the telopeptide region and a hydroxylysyl residue in the conserved triple helical region, and the amount of cross-linking increases with the age of the individual.

The intact triple helical domain of collagen is resistant to almost all enzymes except mammalian collagenase which cleaves most collagens into a three-quarter length TcA fragment and a one-quarter length TcB fragment. However, upon heating, the triple helix is denatured and thus susceptible to non-specific proteinases. Cleavage of collagen with cyanogen bromide, which cleaves at the carboxyl terminal of methionine residues, produces a unique set of peptides, called CB peptides, which can be purified by a combination of ion-exchange and molecule sieve chromatography (Piez, 1976). For type I collagen, CB peptides have been numbered using rat collagen as the standard, and for type II collagen, CB peptides have been numbered using chick collagen as the standard. When a methionine cleavage site is missing as may occur in collagen of another species, the numbers designating the 2 uncleaved peptides are both used, separated by a comma (see FIG. 1). Separated α-chains and CB peptides are able to renature, under appropriate conditions, to their original triple-helical conformation (Terato et al, 1985). CB-peptides of type II and type II collagen are particularly amenable to renaturation when separated, because in each type the three α-chains are identical (Terato et al, 1985, Werkmeister and Ramshaw, 1991).

As noted above, the type II collagen molecule consists of three chains wound in a triple helix, and techniques do not yet exist that allow production of a "native" type II collagen molecule by genetic engineering from cDNA constructs. For this reason, measurement of antibodies to collagen requires the use of collagen purified from cartilage, whether of human or animal origin, or purified from chondrosarcoma cell lines. However, since most healthy people have low levels of natural antibody to collagen in their serum, perhaps representing a response to dietary collagens, tests designed to measure antibodies to collagen in rheumatoid arthritis using the entire molecule of purified collagen will not necessarily give disease-specific results. Thus, it is preferable to identify regions of the collagen molecule that react specifically with antibodies in sera of patients with rheumatoid arthritis.

Figure 1:
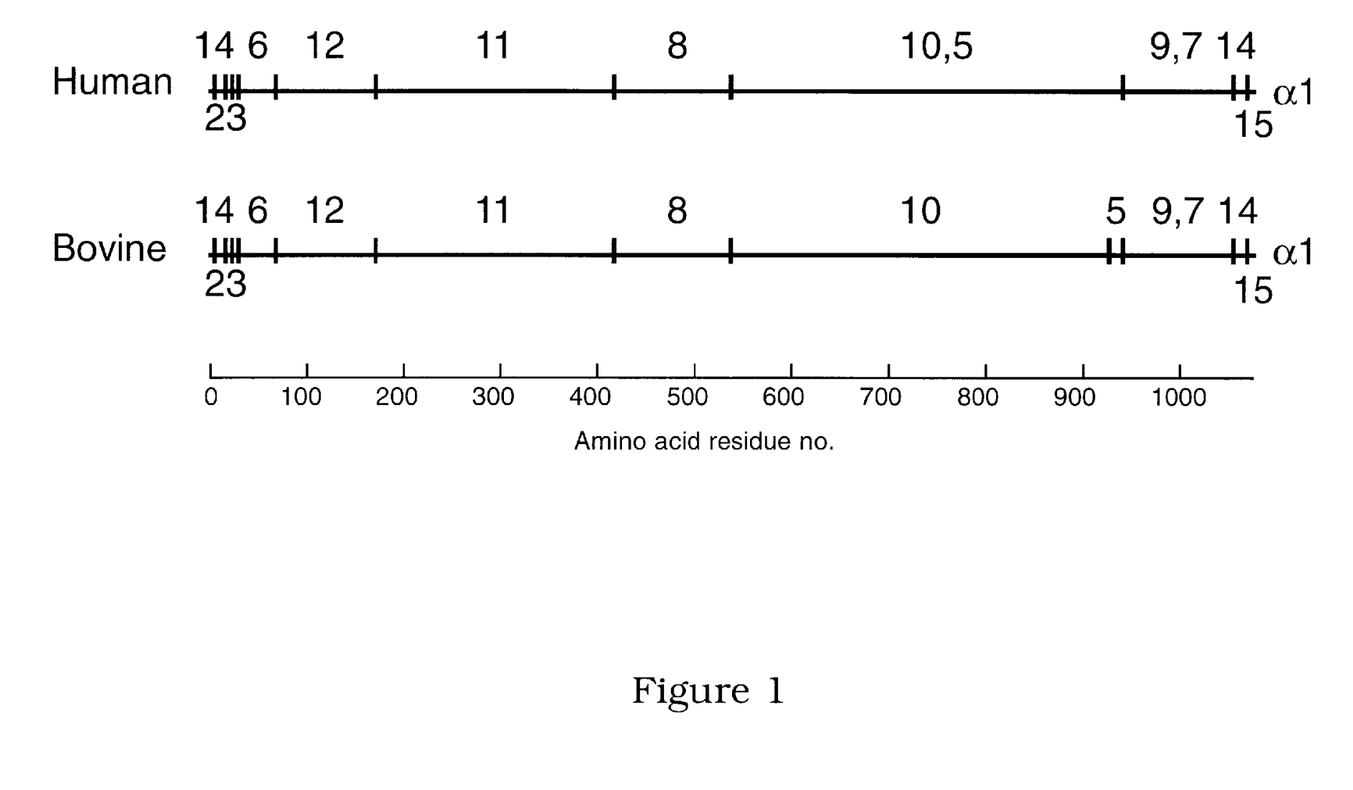
FIG. 1 shows the location and number of the CB peptides for the α1 chain of human type II collagen and the α1 chain of bovine type II collagen. CB peptides have been numbered using chick collagen as the standard. Arrows represent methionine residues in the human type II sequence and the bovine type II sequence which are the sites of cleavage by cyanogen bromide.

In the work leading to the present invention, the regions of the collagen molecule (epitopes) that are recognized by antibodies to collagen have been examined by Western blotting, using cyanogen bromide digests of collagen, whereby the collagen molecule is cleaved at methionine residues, to produce a number of CB peptides (see FIG. 1). Most studies on antibodies to CB peptides of collagen in rheumatoid arthritis disclose responses to multiple peptides (Terato et al, 1990; Buckee et al, 1990; Rowley et al, 1992; Cook et al, 1994). In the past, however, no significant difference has been found in the pattern of recognition of CB peptides by patients with rheumatoid arthritis or other diseases (Rowley et al, 1992), except that antibodies to type II collagen in the inflammatory disease of cartilage, relapsing polychrondritis, react with one of the smaller CB polypeptides of collagen, CB9,7, which is rarely recognized by patients with rheumatoid arthritis (Terato et al, 1990).

SUMMARY OF THE INVENTION

In a first aspect, the present invention provides a method for the detection of antibodies to collagen in a biological sample from a patient, the method comprising contacting said biological sample with an antigen comprising the CB10 peptide of mammalian type II collagen, or an antibody-binding fragment or variant thereof, for a time and under conditions for an antibody-antigen complex to form, and then detecting said complex.

It will, of course, be apparent to persons skilled in this art based on the disclosure herein that the detection of an antibody-antigen complex in accordance with the method of this invention is an indicator of rheumatoid arthritis in the patient, and whilst there is no simple definitive test for rheumatoid arthritis, the method of this invention enables the detection of antibodies to collagen as a predictive marker of early rheumatoid arthritis.

The antigen used in the method of the present invention comprises the CB10 peptide of mammalian type II collagen, or an antibody-binding fragment or variant thereof, from any suitable source, particularly bovine or human type II collagen. The CB10 peptide, or antibody-binding fragment thereof, may be produced by cleavage of the whole collagen molecule with cyanogen bromide, followed by purification of the CB10 fraction, as is well known in the art. Alternatively, however, a similar fraction of the collagen molecule may be prepared by other protein chemistry techniques, including solid phase and other protein synthesis techniques.

The method of the present invention utilises an immunoassay format, including for example an ELISA format, which is well known to persons skilled in this art.

The present invention also extends in another aspect to a diagnostic kit for the detection of antibodies to collagen in a biological sample from a patient, which comprises, in compartmental form, an antigenic preparation comprising the CB10 peptide of mammalian type II collagen, or an antibody-binding fragment or variant thereof, and means for detection of a complex formed between said antigen and antibodies to collagen in said biological sample.

Preferably, the biological sample is a serum, plasma or whole blood sample from the patient. Preferably also, the biological sample is taken from a human patient.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

DETAILED DESCRIPTION OF THE INVENTION

The diagnosis of rheumatoid arthritis in its early stages is difficult. Until characteristic signs of cartilage and bone destruction appear on X-rays, rheumatoid arthritis cannot be reliably distinguished from certain limited forms of arthritis which are of different pathogenesis. Traditionally aspirin and/or other non-steroidal anti-flammatory drugs are given as a first-line of treatment for rheumatoid arthritis, and more potent agents are added if and when the disease deteriorates. However this sequence of treatment does not optimally halt progressive bone and joint destruction. Because the greatest loss of function occurs early in the disease, progressively within the first four years, rheumatologists now believe that giving the most powerful drugs early in the course of treatment is more likely to prevent the destruction that leads to crippling disability. However, since these potent disease-modifying drugs can have significant adverse effects, a marker to distinguish those patients who will develop crippling disease is urgently needed. As noted previously, there have now been several studies that suggest that antibodies to collagen are present very early in rheumatoid arthritis, before the diagnosis is clearly established, and before irreversible joint destruction will have occurred. Accordingly, a method of measuring collagen antibodies that can be reliably performed in routine diagnostic laboratories would have considerable utility.

Most current immunoassays to detect to the entire type II collagen molecule antibodies do not show sufficient specificity and sensitivity for the diagnosis of rheumatoid arthritis, noting that these antibodies may be demonstrable in other diseases, or even in healthy individuals, or may be lacking in cases of established rheumatoid arthritis particularly cases of long duration.

In accordance with the present invention, it has now been shown that the use of the particular CB peptide, CB10 of mammalian type II collagen, or an antibody-binding fragment or variant thereof, instead of the entire collagen molecule, provides for an immunoassay to detect antibodies to collagen that greatly increases the specificity and sensitivity of the immunoassay as a diagnostic test for rheumatoid arthritis.

An "antibody-binding fragment" or variant thereof contemplated by the present invention includes a fragment of the CB10 peptide of a mammalian type II collagen comprising at least 50% of the sequence of said CB10 peptide. Preferably, the percentage of the CB10 sequence is at least about 60%, more preferably at least about 70%, even more preferably at least about 80% and still even more preferably at least about 90% or greater. Such a fragment could be prepared from collagen purified from cartilage, or expressed as a recombinant protein in an appropriate expression system, or derived by any other means. Most preferably said fragment exhibits the helical structure of the CB10 peptide and retains the ability to bind to collagen antibodies. Suitable antibody-binding fragments may be identified by simple trials to ascertain their ability to bind to collagen antibodies.

The present invention also extends to the use of variants of the CB10 peptide or antibody-binding fragment thereof as described above, particularly substitution variants which are conservative in nature and result from replacing one amino acid in the naturally-occurring CB10 amino acid sequence with another having similar structural and/or chemical properties, such as the replacement of a leucine with an isoleucine or valine, an aspartate with a glutamate, or a threonine with a serine. Other suitable variants of the naturally-occurring sequence include insertion or deletion variants, typically of from about one to five amino acids. Suitable variants will preferably exhibit the helical structure of the CB10 peptide and retain the ability to bind to collagen antibodies, and may be identified by simple antibody-binding trials.

The detection of the presence of antibodies to collagen in accordance with the present invention may be accomplished in a number of immunoassay procedures, such as by ELISA procedures. A wide range of immunoassay techniques is available as can be seen by reference to standard immunoassay textbooks. These, of course, include both singlesite and two-site or "sandwich" assays of the non-competitive types, as well as the traditional competitive binding assays.

Sandwich assays are among the most useful and commonly used assays and are favoured for use in the present invention. A number of variations of the sandwich assay technique exist, and all are intended to be encompassed by the present invention. Briefly, in a typical assay to detect antibodies in a sample, an unlabelled antigen is immobilized on a solid substrate and the sample to be tested brought into contact with the bound antigen molecule. After a suitable period of incubation, for a period of time sufficient to allow formation of an antibody-antigen complex, a second antibody such as anti-human IgG, labelled with a reporter molecule capable of producing a detectable signal, is then added and incubated, allowing time sufficient for the formation of another complex of antibody:antigen:labelled antibody. Any unreacted material is washed away, and the presence of the antibody to be detected in the sample is determined by observation of a signal produced by the reporter molecule. The results may either be qualitative, by simple observation of the visible signal, or may be quantitated by comparing with a control sample containing known amounts of the antibody to be detected. Variations on this assay include a simultaneous assay, in which both sample and labelled antibody are added simultaneously to the bound antigen. These techniques are well known to those skilled in the art, including any minor variations as will be readily apparent.

In the typical sandwich assay, antigen is immobilised, for example by being either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs, or microplates, or any other surface suitable for conducting an immunoassay. The binding processes are well-known in the art and generally consist of crosslinking, covalent binding or physical adsorption. The immobilised antigen is then washed in preparation for the test sample. An aliquot of the sample to be tested is then contacted with the immobilised antigen and incubated for a period of time sufficient (e.g. 2–40 minutes) and under suitable conditions (e.g. 25° C.) to allow binding of any antibody to collagen present in the sample. Following the incubation period, the immobilised antigen with any bound antibody is washed and dried, and incubated with a second antibody specific for the bound antibody, for example anti-human IgG. The second antibody is linked to a reporter molecule which is used to indicate the binding of the second antibody to the antibody:immobilised antigen complex.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide-containing molecules (i.e. radioisotopes), or chemiluminescent molecules. In the case of an enzyme immunoassay (EIA), an enzyme is conjugated to the second antibody, generally by means of glutaraldehyde or periodate. As will be readily recognized, however, a wide variety of different conjugation techniques exist, which are readily available to the skilled artisan. Commonly used reporter enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product rather than the chromogenic substrates noted above. In all cases, the enzyme-labelled antibody is added to the first antibody-antigen complex, allowed to bind, and then the excess reagent is washed away. A solution containing the appropriate substrate is then added to the complex of antibody:antigen:labelled antibody. The substrate will react with the enzyme linked to the second antibody, giving a qualitative visual signal, which may be further quantitated, usually using a spectrophotometric instrument, to give an indication of the amount of antibody which was present in the sample. "Reporter molecule" also extends to use of cell agglutination or inhibition of agglutination, such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochromelabelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-antigen complex. After washing off the unbound reagent, the remaining tertiary complex is then exposed to light of the appropriate wavelength and the fluorescence observed indicates the presence of the antibody of interest. Immunofluorescence and EIA techniques are both very well established in the art and are particularly preferred for the present method. However, other reporter molecules, such as radioisotope, chemiluminescent or bioluminescent molecules, may also be employed.

Further features of the present invention are more fully described in the following Examples. It is to be understood, however, that this detailed description is included solely for the purposes of exemplifying the present invention, and should not be understood in any way as a restriction on the broad description of the invention as set out above.

EXAMPLE 1

A. Techniques Used

Standard Method of Purification of Peptides of Collagen

Human and bovine type II collagen was prepared from cartilage by pepsin digestion and differential salt precipitation (Rowley, et al., 1988). Bovine type II collagen was digested with cyanogen bromide (CNBr) and the resultant fragments of type II collagen, known as CB peptides, were purified according to the method of Miller and Lunde (1973) with slight modifications; 1.5 g of bovine type II collagen was dissolved in a minimum volume of 70% (v/v) formic acid, containing 1.5 g of CNBr (Sigma, St Louis Mo., USA) and cleavage was achieved by the method of Scott and Veis (1976).

Figure 2A:
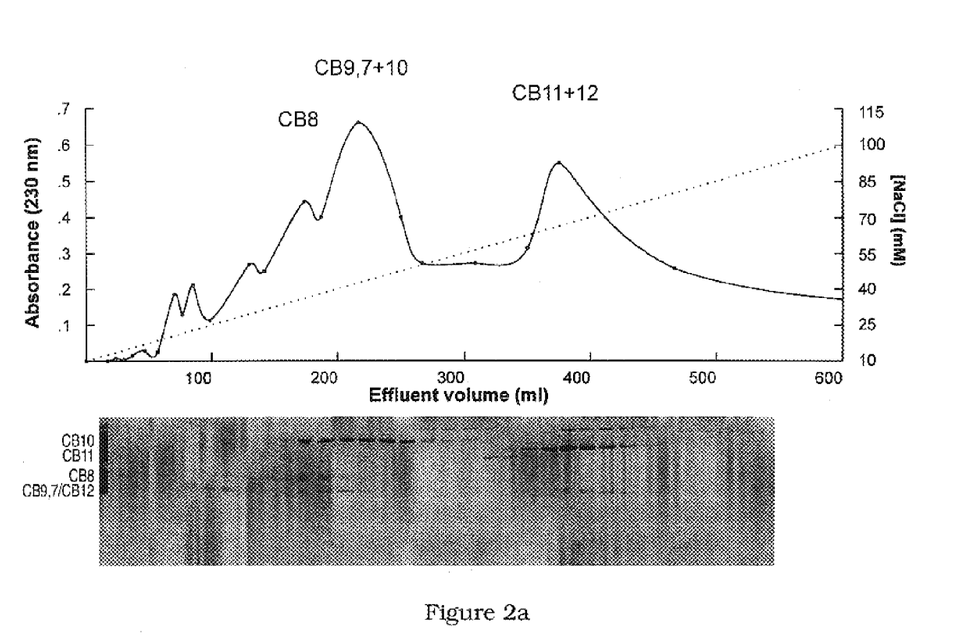
FIG. 2a show a carboxymethylcellulose (CM-cellulose) chromatogram and corresponding Coomassie blue protein stain illustrating the separation of the CB peptides of bovine type II collagen, using a linear salt gradient ( . . . ).
Figure 2B:
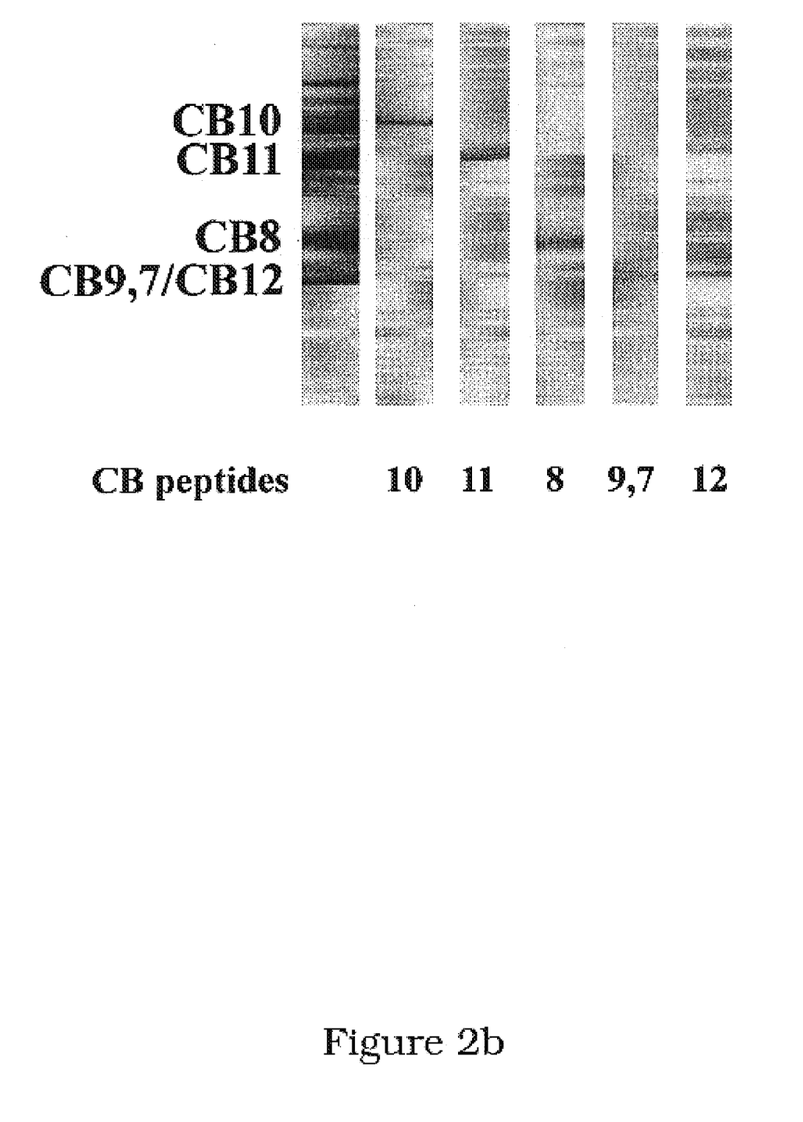
FIG. 2b shows Coomassie blue stained gels of purified fractions from the CM-cellulose column containing various CB peptides, including CB10 and CB11, of bovine type II collagen.

The CB peptides were initially resolved into 2 major fractions by chromatography on a 2.4×82 cm column of Bio-Gel P-2 (100–200 mesh, exclusion limit 2600 daltons, globular proteins, Biorad, USA) equilibrated with 0.1 M acetic acid. The peptides obtained after cyanogen bromide digestion were dissolved in 12 ml of 0.1 M acetic acid and 3 ml (500 mg) was applied to the column at a time. The larger peptides, eluted in the excluded volume of the P-2 column, were pooled, lyophilized, and rechromatographed on a 2.5×12 cm cation exchange column of carboxymethylcellulose (CM-cellulose, Whatman CM-52). The column was equilibrated with 0.02 M sodium citrate, pH 3.6 containing 0.01 M NaCl, designated as the start buffer, and the peptides were dissolved in this start buffer for application to the column. Chromatography was performed at 42° C. over 10 hours using a linear salt gradient obtained by the addition of 1% 0.16 M NaCl in 0.02 M sodium citrate, pH 3.6, to the start buffer every 6 minutes, with a flow rate of 1.75 ml/mm, using the Biorad Econo system (Biorad, USA). Fractions of 17 ml were collected at 10 minute intervals, and were run on 15% tricine gels and stained with 0.2% (w/v) Coomassie Blue (Biorad, USA). Fractions containing CB10 identified by comparison with published type II CB peptide maps (Bornstein et al, 1980; Miller et al, 1982) were pooled, as were fractions containing CB11, desalted on the Bio-Gel P-2 column and lyophilized. CB10 was purified further, and in particular separated from CB8 and CB9,7, and CB11 was separated from CB12, by applying each fraction to a 1.0×75 cm column of P-30 (100–200 mesh, exclusion limit 40 kD, globular proteins, Biorad, USA) equilibrated in 0.1 M acetic acid. The purity of the peptides after each column run was determined by separation on 15% tricine gels and staining with 0.2% (w/v) Coomassie blue (FIGS. 2a, 2b).

Purified CB10 and CB11 were renatured by step-wise cooling from 20° C. to 0.2° C., as described by Terato et al, 1985.

Measurement by ELISA of Antibodies to Native Type II Collagen

Antibodies to native human type II collagen, and native bovine type II collagen, were measured by an enzyme linked immunosorbent assay (ELISA). Microtitre plates (Dynatech, Germany) were coated with 100 μl/well of 10 μg/ml human or bovine type II collagen overnight at 4° C. Plates were washed 3 times in 1% (w/v) skim-milk powder in PBS, pH 7.4 (SM-PBS) containing 0.05% Tween 20 (Sigma, USA) and 3 times in distilled water (dH$_2$O), blocked with 1% SM-PBS, 0.05% Tween 20 for 2 hours at room temperature, then washed again as above. Sera were tested in duplicate at a dilution of 1:50 in the presence or absence of antigen. Antibodies were detected using horseradish peroxidase conjugate (HRP) anti-human IgG (Silenus, Hawthorn, Australia), with 0.5 mg/ml 2,2-azino-di-[3-:ethyl-benzthiazoline sulfonate (6)] (ABTS) (Boehringer, Germany) in 0.03 M citric acid, 0.04 M Na$_2$HPO$_4$, 0.003% H$_2$O$_2$, pH 4 as substrate. Plates were read after 30 minutes at 41 5 nm on a Biorad platereader (Biorad, USA). Non-specific binding of immunoglobulins to the plates was allowed for by subtracting the optical density (OD) obtained in the absence of collagen from that obtained in wells coated with collagen.

Sera from two patients with high levels of antibodies to native and denatured type II collagen, were used throughout as positive controls.

Measurements by ELISA of Antibodies to Purified CB Peptides of Type II Collagen

Antibodies to the purified CB 10 peptide of bovine type II collagen were measured by ELISA as described above for intact type II collagen with the following modifications. Plates were coated with 100 μl of 10 μg/ml of purified CB10 peptide and sera were tested at a dilution of 1:50. The peptide antigen was coated onto the plates overnight at 4° C., blocked with 1% SM-PBS, 0.05% Tween 20 for 90 minutes at room temperature with shaking, and sera were incubated for 2 hours at room temperature with shaking. Plates were washed 3 times in tris buffered saline (TBS) containing 0.05% Tween 20 using an automatic plate washer (Wallac, Finland) in all steps prior to the addition of the secondary antibody and in distilled water) immediately before and in all steps subsequent to the addition of the secondary antibody. Bound antibodies were detected using HRP-conjugated anti-human IgG (Silenus, Hawthorn, Australia), and the appropriate substrate. Results are expressed in terms of the number of standard deviations above the mean for controls as described above.

B. Results

Antibodies to Type II Collagen

Figure 3:
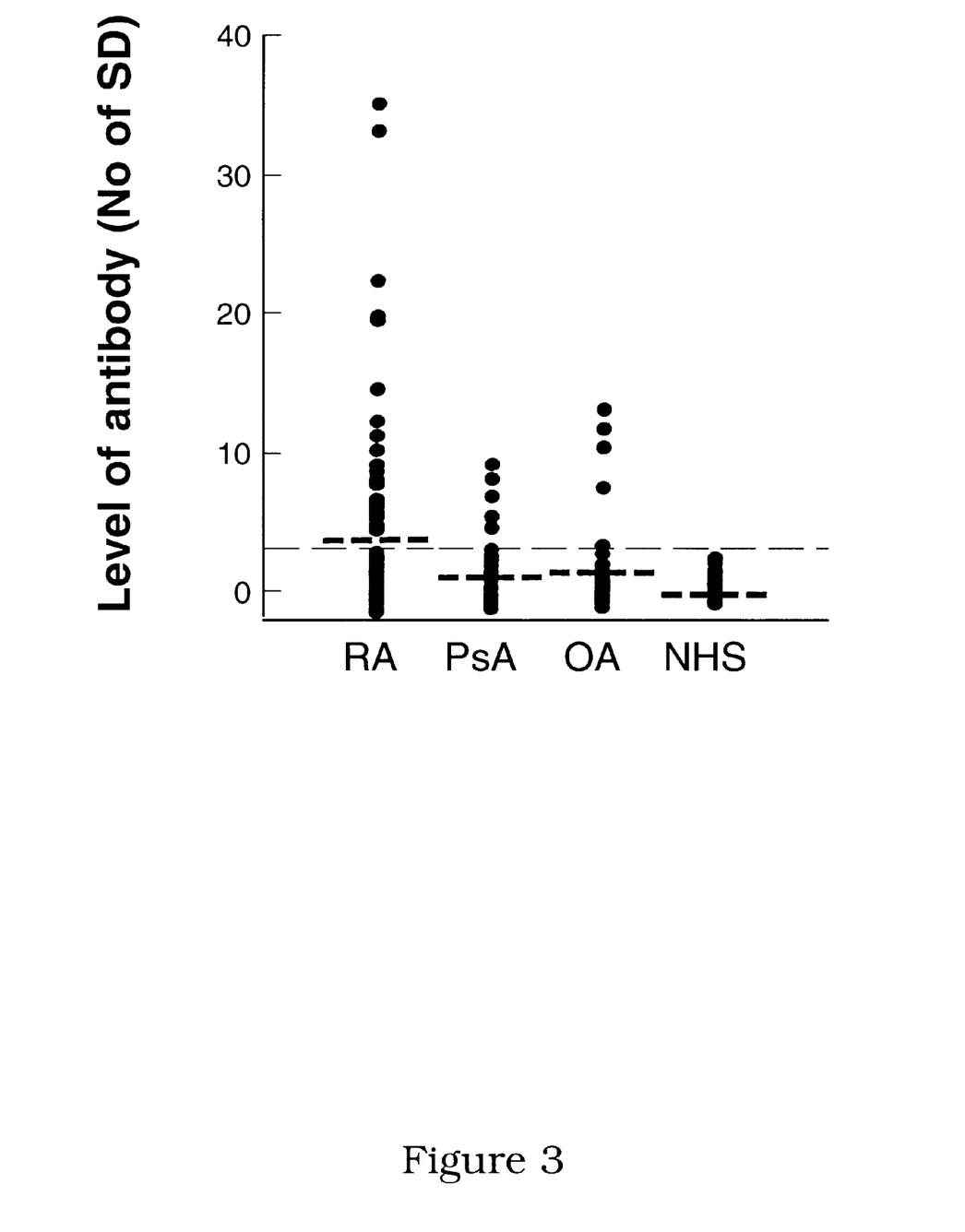
FIG. 3 shows the levels of IgG antibodies to human type II collagen in patients with rheumatoid arthritis (RA), psoriatic arthritis (PsA), and osteoarthritis (OA), and in normal human sera (NHS). Results are expressed as the number of standard deviations (SD) above the mean level of antibody in normal sera. A serum is regarded as giving a positive test result if the level of antibody is greater than 3 SD above the mean (—). The thick dashed line represents the mean level of antibody for each group of patients.

Antibodies to intact human type II collagen measured by ELISA were present in sera of 25% of 96 patients with rheumatoid arthritis. By contrast, antibodies to collagen were present in 15% of 34 patients with osteoarthritis and in 15% of 33 patients with inflammatory arthritis associated with psoriasis (psoriatic arthritis), representing other non-autoimmune articular diseases. These figures are comparable with those reported by others for rheumatoid arthritis and other articular disease using an ELISA in a similar format (Choi et al., 1988; Fujii et al., 1992). The levels as well as frequencies of antibodies to type II collagen were generally higher in rheumatoid arthritis than in other diseases (FIG. 3).

Antibodies to Collagen CB10 Peptide

Figure 4:
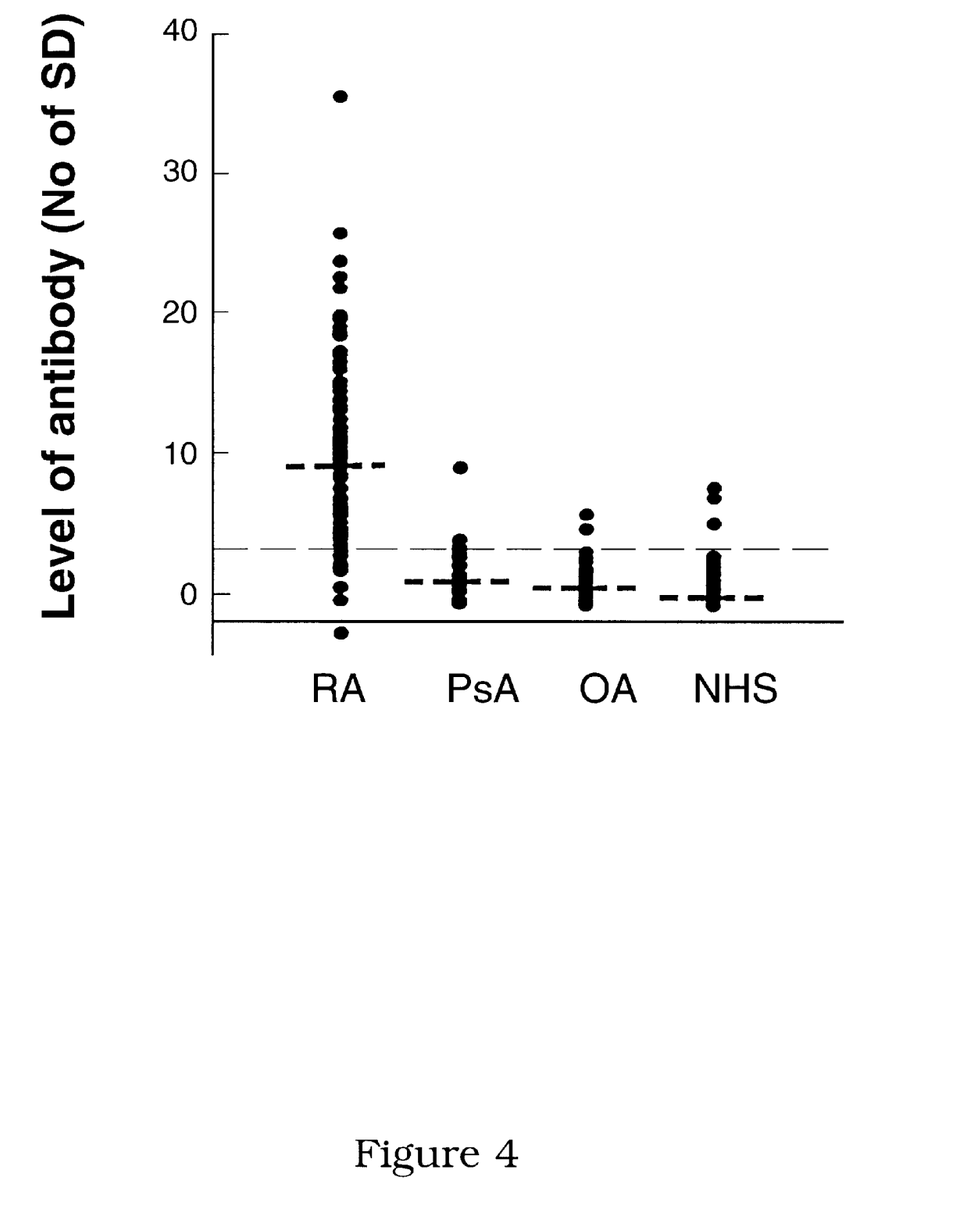
FIG. 4 shows the levels of antibodies to the CB10 peptide of bovine type II collagen in patients with rheumatoid arthritis (RA), psoriatic arthritis (PsA), and osteoarthritis (OA), and in normal human sera (NHS). Results are expressed as the number of standard deviation (SD) above the mean level of antibody in normal sera. A serum is regarded as giving a positive test result if the level of antibody is greater than 3 SD above the mean (—). The thick dashed line represents the mean level of antibody for each group of patients.

FIG. 4 compares the frequency of antibodies tested in a similar ELISA in which CB10 peptide prepared from bovine type II collagen was used as antigen. Antibodies to the CB10 peptide of bovine type II collagen were present in the sera of 88% of the same 96 patients with rheumatoid arthritis, but in 6% of patients with osteoarthritis and in 12% of patients with psoriatic arthritis. In other words, the replacement of the intact type II by the CB10 peptide greatly increased the sensitivity of the assay for the diagnosis of rheumatoid arthritis, from 25% to 88%, without any decrease in specificity, since the frequency of positive reactions to the CB10 peptide in the sera from patients with diseases of the joint other than rheumatoid arthritis was no greater than the frequency of positive reactions to intact type II collagen, i.e. less than 15%.

This increased sensitivity was shown not to be due to the use of bovine (versus human) CB10 peptide of collagen in the assay, since the frequency of reactivity by ELISA with intact collagen is very similar whether bovine collagen or human collagen is used as antigen in the ELISA (see Table I below). In addition, there was substantial specificity to the reactivity against CB10 since reactivity observed in rheumatoid arthritis with the CB11 peptide, a peptide of collagen of very similar size, was only 50%.

TABLE 1

| Group | No. | Antibody to intact human type II collagen | Antibody to intact bovine type II collagen | Antibody to bovine CB10 | Antibody to bovine CB11 |
|---|---|---|---|---|---|
| Rheumatoid arthritis | 96 | 24 (25%) | 23 (24%) | 84 (88%) | 48 (50%) |
| Osteoarthritis | 34 | 5 (15%) | 3 (10%) | 2 (6%) | 7 (21%) |
| Psoriatic arthritis | 33 | 5 (15%) | 9 (27%) | 4 (12%) | 2 (6%) |
| Normal human serum | 93 | 0 | 1 (1%) | 3 (3%) | 2 (2%) |

REFERENCES:

Bornstein, P. and Sage, H. (1980). Structurally distinct collagen types. *Ann. Rev. Biochem.* 49:957–1003.

Brodsky, B. and Shah, N.K. (1995). The triple-helix motif in proteins *FASEB J.* 9:1537–1546.

Buckee, C., Morgan, K., Ayad, S., Collins, I., Clague, R. B., Holt, P. J. L. (1990). Diversity of antibodies to type II collagen in patients with rheumatoid arthritis: detection by binding to α-chains and to cyanogen bromide peptides. *Brit. J. Rheumatol.* 29:254–258.

Charriere, G., Hartmann, D. J., Vignon, E., Ronziere, M-C., Herbage, D., Ville, G. (1988). Antibodies to types I, II, IX, and XI collagen in the serum of patients with rheumatic diseases. *Arthritis Rheum.* 31:325–332.

Choi, E. K. K., Gatenby, P. A., McGill, N. W., Bateman, J. F., Cole, W. G., York, J. R. (1988). Autoantibodies to type II collagen: occurrence in rheumatoid arthritis, other arthritides, autoimmune connective diseases, and chronic inflammatory syndromes. *Ann. Rheum. Dis.* 47:313–322.

Clague, R. B., Shaw, M. J., Holt, P. J. L. (1980). Incidence of serum antibodies to native type I and type II collagens in patients with inflammatory arthritis. *Ann. Rheum. Dis.* 39:201–206.

Collier, D. H., Kerwar, S. S., Garovoy, M. R., Fyfe, K. H., Stobo, J. D. (1984). Anticollagen antibodies and immune response gene products in rheumatoid arthritis. *Arthritis Rheum.* 27:1201–1209.

Cook, A. D., Rowley, M. J., Stockman, A., Muirden, K. D., Mackay, I. R. (1994). Specificity of antibodies to type II collagen in early rheumatoid arthritis. *J. Rheumatol.* 21:1186–1191.

Cook, A. D., Rowley, M. J., Mackay, I. R., Cough, A., Emery, P. (1996). Antibodies to type II collagen in early rheumatoid arthritis: correlation with disease progression. *Arthritis Rheum.* 39:1720–1727.

Courtney, J. S., Dallman, M. J., Dayan, A. D., Martin, A., Mosedale, B. (1980). Immunization against heterologous type II collagen induces arthritis in mice. *Nature* 283:666–667.

Fujii, K., Tsuji, M., Kimamura, A., Murota, K. (1992). The diagnostic significance of anti-type II collagen antibody assay in rheumatoid arthritis. *Int. Orthop.* 16:272–276.

Gay, S., Gay, R. E. and Miller, E. F. (1980). The collagens of the joint. *Arthritis Rheum.* 23:937–941.

Gioud, M., Meghliaoui, A., Costa, O., Monier, J. C. (1982). Antibodies to native type I and II collagens detected by an enzyme linked immunosorbent assay (ELISA) in rheumatoid arthritis and systemic lupus erythematosus. *Collagen Rel. Res.* 2:557–564.

Heinegard, D. and Poulsson, M. (1987). *Methods Enzymol.* 145:336–363.

Hochberg, M. C. (1981). Adult and juvenile rheumatoid arthritis: current epidemiologic concepts. *Epidemiol. Rev.* 3:27–44.

Miller, E. J. (1985). The structure of fibril-forming collagens. *Ann. N.Y. Acad.Sci.* 460:1–13.

Miller, E. J. and Lunde, L. G. (1973). Isolation and characterization of the cyanogen bromide peptides from the alpha-1 (II) chain of bovine and human cartilage collagen. *Biochem* 12:3153–3159.

Miller, E. J. and Rhodes, R. K. (1982). Preparation and characterization of the different types of collagen. *Meth. Enzymol.* 82:33–64.

Morgan, K., Clague, R. B., Collins, I., Ayad, S., Phinn, S. D., Holt, P. J. L. (1987). Incidence of antibodies to native and denatured cartilage collagens (types II, IX, and XI) and to type I collagen in rheumatoid arthritis. *Ann. Rheum. Dis.* 46:902–907.

Morgan, K., Clague, R. B., Collins, I., Ayad, S., Phinn, S. D., Holt, P. J. L. (1989). A longitudinal study of anticollagen antibodies in patients with rheumatoid arthritis. *Arthritis Rheum.* 32:139–145.

Pereira, R. S., Black, C. M., Duance, V. C., Jones, V. E., Jacoby, R. K., Welsh, L. I. (1985). Disappearing collagen antibodies in rheumatoid arthritis. *Lancet ii*:501–502.

Piez, K. A. (1976). Primary structure. In Biochemistry of collagen. Ramchandran, G. H. and Reddi, A. N. (eds). Plenum, New York, pp 1–44.

Piez, K. A. (1982). Structure and assembly of the native collagen fibril. Connect Tissue Res. 10:25–36.

Rosenberg, A. M., Hunt, D. W. C., Petty, R. E. (1984). Antibodies to native and denatured type II collagen in children with rheumatic diseases. *J. Rheumatol.* 11:425–431.

Rowley, M. J., Gershwin, M. E., Mackay, I. R. (1988). Collagen antibodies in juvenile arthritis and adult rheumatoid arthritis: differences in levels and type-specificity. *J. Rheumatol.* 15:289–294.

Rowley, M. J., Mackay, I. R., Brand, C. A., Bateman, J. F., Chan, D. (1992). Epitope specificity of antibodies to type II collagen in rheumatoid arthritis and systemic lupus erythematosus. *Rheumatol. Int.* 12:65–69.

Scott, P. G. and Veis, A. (1976). The cyanogen bromide peptides of bovine soluble and insoluble collagens. *Connect Tissue Res.* 4:107–116.

Stuart, K. M., Huffstutter, E. H., Townes, A. S., Kang, A. H. (1983). Incidence and specificity of antibodies to types I, II, III, IV and V collagen in rheumatoid arthritis and other rheumatic diseases as measured by $^{125}$I-radioimmunoassay. *Arthritis Rheum.* 27:1201–1209.

Steffen, C., Timpl R. (1963). Antigenicity of collagen and its application in the serologic investigation of rheumatoid arthritis sera. *Int. Arch. Allergy Appl. Immunol.* 22:333–349.

Stockman, A., Rowley, M. J., Emery, P., Miurden, K. D. (1989). Activity of rheumatoid arthritis and levels of coliagen antibodies: a prospective study. *Rheumatol. Int.* 8:239–243.

Terato, K., Cremer, M. A., Hasty, K. A., Kang, A. H., Hasty, D. L., Townes, A. S. (1985). Physicochemical and immunological studies of the renatured alpha 1(II) chains and isolated cyanogen bromide peptides of type II collagen. *Coll. Rel. Res.* 5:469–480.

Terato, K., Shimozuru, Y., Katayama, K., Takemitsu, Y., Yamashita, I., Miyatsu, M., Fujii, K., Sagara, M., Kobayashi, S., Goto, M., Nishioka, K., Miyatsaka, N., Nagai, Y. (1990). Specificity of antibodies to type II collagen in rheumatoid arthritis. *Arthritis Rheum.* 32:748–758.

Trentham, D. E. Townes, A. S., Kang, A. H. (1977). Autoimmunity to type II collagen: an experimental model of arthritis. *J. Exp. Med.* 146:857–868.

Trentham, D. E. Kammer, G. M., McCune, W. J., David, J. R. (1981). Autoimmunity to collagen. A shared feature of psoriatic and rheumatoid arthritis. *Arthritis Rheum.* 24:1363–1369.

Werkmeister, J. A., Ramshaw, J. A. (1991). Multiple antigenic determinants on type III collagen. *Biochem J.* 274:544–551.

---

What is claimed is:

1. A method for detecting antibodies to collagen in a biological sample from a mammal to indicate rheumatoid arthritis comprising (i) providing an antigen comprising the CB10 peptide of mammalian type II collagen, (ii) contacting a biological sample from said mammal with said antigen or an antibody-binding fragment thereof, for a time and under conditions for an antibody-antigen complex to form, then (iii) detecting whether an antibody-antigen complex forms, indicating development of rheumatoid arthritis in said mammal.

2. The method of claim 1, wherein the CB10 peptide, or an antibody-binding fragment thereof, is from a bovine source.

3. The method of claim 1, wherein the CB10 peptide, or an antibody-binding fragment thereof, is from a human source.

4. The method of claim 1, wherein the CB10 peptide, or an antibody-binding fragment thereof, is produced by cleavage of the whole collagen molecule with cyanogen bromide, followed by purification of the CB10 fraction.

5. The method of claim 1, wherein the detection of said antibody-antigen complex is by immunoassay.

6. The method of claim 5, wherein the immunoassay is an ELISA.

7. The method of claim 1, wherein the biological sample is serum, plasma or whole blood.

8. The method of claim 1, wherein the biological sample is taken from a human patient.

9. The method of claim 1, wherein the antigen is immobilised by being bound to a solid surface.

10. The method of claim 9, wherein the detecting of said antibody-antigen complex comprises incubating said complex with a second antibody specific for the bound antibody, said second antibody being linked to a reporter molecule which is used to indicate the binding of the second antibody to the antibody:immobilised antigen complex.

11. The method of claim 10, wherein the second antibody is anti-human IgG.

12. The method of claim 10, wherein the reporter molecule provides an identifiable signal which allows the detection of binding of the second antibody to the antibody:immobilised antigen complex.

\* \* \* \* \*

SEQUENCE LISTING

<160> NUMBER OF SEQ ID NOS: 1

<210> SEQ ID NO 1
<211> LENGTH: 347
<212> TYPE: PRT
<213> ORGANISM: Homo sapiens

<400> SEQUENCE: 1

Met Pro Gly Glu Arg Gly Ala Ala Gly Ile Ala Gly Pro Lys Gly Asp
 1               5                   10                  15

```
-continued

Arg Gly Asp Val Gly Glu Lys Gly Pro Glu Gly Ala Pro Gly Lys Asp
             20                  25                  30

Gly Gly Arg Gly Leu Thr Gly Pro Ile Gly Pro Pro Gly Pro Ala Gly
         35                  40                  45

Ala Asn Gly Glu Lys Gly Glu Val Gly Pro Pro Gly Pro Ala Gly Ser
     50                  55                  60

Ala Gly Ala Arg Gly Ala Pro Gly Glu Arg Gly Glu Thr Gly Pro Pro
 65              70                  75                      80

Gly Thr Ser Gly Ile Ala Gly Pro Pro Gly Ala Asp Gly Gln Pro Gly
                 85                  90                  95

Ala Lys Gly Glu Gln Gly Glu Ala Gly Gln Lys Gly Asp Ala Gly Ala
             100                 105                 110

Pro Gly Pro Gln Gly Pro Ser Gly Ala Pro Gly Pro Gln Gly Pro Thr
             115                 120                 125

Gly Val Thr Gly Pro Lys Gly Ala Arg Gly Ala Gln Gly Pro Pro Gly
         130                 135                 140

Ala Thr Gly Phe Pro Gly Ala Ala Gly Arg Val Gly Pro Pro Gly Ser
145              150                 155                 160

Asn Gly Asn Pro Gly Pro Pro Gly Pro Pro Gly Pro Ser Gly Lys Asp
             165                 170                 175

Gly Pro Lys Gly Ala Arg Gly Asp Ser Gly Pro Pro Gly Arg Ala Gly
             180                 185                 190

Glu Pro Gly Leu Gln Gly Pro Ala Gly Pro Pro Gly Glu Lys Gly Glu
         195                 200                 205

Pro Gly Asp Asp Gly Pro Ser Gly Ala Glu Gly Pro Pro Gly Pro Gln
         210                 215                 220

Gly Leu Ala Gly Gln Arg Gly Ile Val Gly Leu Pro Gly Gln Arg Gly
225              230                 235                 240

Glu Arg Gly Phe Pro Gly Leu Pro Gly Pro Ser Gly Glu Pro Gly Gln
             245                 250                 255

Gln Gly Ala Pro Gly Ala Ser Gly Asp Arg Gly Pro Pro Gly Pro Val
             260                 265                 270

Gly Pro Pro Gly Leu Thr Gly Pro Ala Gly Glu Pro Gly Arg Glu Gly
         275                 280                 285

Ser Pro Gly Ala Asp Gly Pro Pro Gly Arg Asp Gly Ala Ala Gly Val
     290                 295                 300

Lys Gly Asp Arg Gly Glu Thr Gly Ala Val Gly Ala Pro Gly Ala Pro
305              310                 315                 320

Gly Pro Pro Gly Ser Pro Gly Pro Ala Gly Pro Thr Gly Lys Gln Gly
             325                 330                 335

Asp Arg Gly Glu Ala Gly Ala Gln Gly Pro Met
             340                 345
```